United States Patent
Pereira Rodriguez et al.

(10) Patent No.: US 9,279,135 B2
(45) Date of Patent: Mar. 8, 2016

(54) KLUYVEROMYCES LACTIS YEAST STRAIN AND METHODS FOR THE PRODUCTION OF SUGARS, ETHANOL, BETA-GALACTOSIDASE AND BIOMASS

(75) Inventors: Angel Pereira Rodriguez, A Coruna (ES); Manuel Becerra Fernandez, A Coruna (ES); Maria Isabel Gonzalez Siso, A Coruna (ES); Maria Esperanza Cerdan Villanueva, A Coruna (ES)

(73) Assignee: QUEIZUAR, S.L., A Coruna (ES)

( * ) Notice: Subject to any disclaimer, the term of this patent is extended or adjusted under 35 U.S.C. 154(b) by 85 days.

(21) Appl. No.: 14/117,448

(22) PCT Filed: Jul. 27, 2011

(86) PCT No.: PCT/ES2011/070550
§ 371 (c)(1),
(2), (4) Date: Aug. 22, 2014

(87) PCT Pub. No.: WO2012/175760
PCT Pub. Date: Dec. 27, 2012

(65) Prior Publication Data
US 2015/0031078 A1     Jan. 29, 2015

(51) Int. Cl.
*C12P 7/06*    (2006.01)
*C12P 19/02*   (2006.01)
*C12R 1/645*   (2006.01)
*C12N 9/38*    (2006.01)

(52) U.S. Cl.
CPC .................. *C12P 7/06* (2013.01); *C12N 9/2471* (2013.01); *C12P 7/065* (2013.01); *C12P 19/02* (2013.01); *C12R 1/645* (2013.01); *Y02E 50/17* (2013.01)

(58) Field of Classification Search
None
See application file for complete search history.

*Primary Examiner* — Michelle K Joike
*Assistant Examiner* — Mindy G Brown
(74) *Attorney, Agent, or Firm* — Lucas & Mercanti, LLP

(57) ABSTRACT

A *Kluyveromyces lactis* yeast strain comprising the sequence identified by SEQ ID NO: 1, and methods for the production of sugars (glucose and galactose), ethanol, β-galactosidase and biomass is provided, in which the *Kluyveromyces lactis* yeast strain is cultured in the presence of a lactose-containing medium. The lactose-containing medium may be milk, whey, whey resulting from the preparation of butter, whey resulting after casein precipitation, milk permeate, whey permeate, acid whey and YPL culture medium.

9 Claims, 3 Drawing Sheets

SEQUENCE LISTING

<160> NUMBER OF SEQ ID NOS: 5

<210> SEQ ID NO 1
<211> LENGTH: 3479
<212> TYPE: DNA
<213> ORGANISM: Artificial Sequence
<220> FEATURE:
<223> OTHER INFORMATION: Kluyveromyces lactis alfa mating factor
      secretion domain, Kluyveromyces lactis beta-galactosidase and FLAG
      peptide
<220> FEATURE:
<221> NAME/KEY: sig_peptide
<222> LOCATION: (14)..(334)
<223> OTHER INFORMATION: Alfa mating factor secretion domain
<220> FEATURE:
<221> NAME/KEY: mat_peptide
<222> LOCATION: (378)..(3476)
<220> FEATURE:
<221> NAME/KEY: CDS
<222> LOCATION: (378)..(3476)
<220> FEATURE:
<221> NAME/KEY: gene
<222> LOCATION: (378)..(3452)
<223> OTHER INFORMATION: Beta-galactosidase
<220> FEATURE:
<221> NAME/KEY: misc_feature
<222> LOCATION: (3453)..(3476)
<223> OTHER INFORMATION: FLAG peptide

<400> SEQUENCE: 1

```
aagcttgaaa aaatgaaat tctctactat attagccgca tctactgctt taatttccgt    60
tgttatggct gctccagttt ctaccgaaac tgacatcgac gatcttccaa tatcggttcc   120
agaagaagcc ttgattggat tcattgactt aaccggggat gaagtttcct tgttgcctgt   180
taataacgga acccacactg gtattctatt cttaaacacc accatcgctg aagctgcttt   240
cgctgacaag gatgatctcg agaaaagaga ggctgaagct agaagagcta gatctcctag   300
gggtaccgtc gacggcgcgc ctgcggccgc gagctcaagc ttgatctttc gctgacaagg   360
atgatctcga gaaaaga atg tct tgc ctt att cct gag aat tta agg aac       410
                    Met Ser Cys Leu Ile Pro Glu Asn Leu Arg Asn
                      1               5                  10 ccc aaa aag gtt cac gaa aat aga ttg cct act agg gct tac tac tat      458
Pro Lys Lys Val His Glu Asn Arg Leu Pro Thr Arg Ala Tyr Tyr Tyr
            15                  20                  25 gat cag gat att ttc gaa tct ctc aat ggg cct tgg gct ttt gcg ttg      506
Asp Gln Asp Ile Phe Glu Ser Leu Asn Gly Pro Trp Ala Phe Ala Leu
        30                  35                  40 ttt gat gca cct ctt gac gct ccg gat gct aag aat tta gac tgg gaa      554
Phe Asp Ala Pro Leu Asp Ala Pro Asp Ala Lys Asn Leu Asp Trp Glu
    45                  50                  55 acg gca aag aaa tgg agc acc att tct gtg cca tcc cat tgg gaa ctt      602
Thr Ala Lys Lys Trp Ser Thr Ile Ser Val Pro Ser His Trp Glu Leu
60                  65                  70                  75 cag gaa gac tgg aag tac ggt aaa cca att tac acg aac gta cag tac      650
Gln Glu Asp Trp Lys Tyr Gly Lys Pro Ile Tyr Thr Asn Val Gln Tyr
                80                  85                  90 cct atc cca atc gac atc cca aat cct ccc act gta aat cct act ggt      698
Pro Ile Pro Ile Asp Ile Pro Asn Pro Pro Thr Val Asn Pro Thr Gly
            95                 100                 105 gtt tat gct aga act ttt gaa tta gat tcg aaa tcg att gag tcg ttc      746
Val Tyr Ala Arg Thr Phe Glu Leu Asp Ser Lys Ser Ile Glu Ser Phe
        110                 115                 120 gag cac aga ttg aga ttt gag ggt gtg gac aat tgt tac gag ctt tat      794
Glu His Arg Leu Arg Phe Glu Gly Val Asp Asn Cys Tyr Glu Leu Tyr
    125                 130                 135
```

```
gtt aat ggt caa tat gtg ggt ttc aat aag ggg tcc cgt aac ggg gct    842
Val Asn Gly Gln Tyr Val Gly Phe Asn Lys Gly Ser Arg Asn Gly Ala
140             145                 150                 155 gaa ttt gat atc caa aag tac gtt tct gag ggc gaa aac tta gtg gtc    890
Glu Phe Asp Ile Gln Lys Tyr Val Ser Glu Gly Glu Asn Leu Val Val
                160                 165                 170 gtc aag gtt ttc aag tgg tcc gat tcc act tat atc gag gac caa gat    938
Val Lys Val Phe Lys Trp Ser Asp Ser Thr Tyr Ile Glu Asp Gln Asp
            175                 180                 185 caa tgg tgg ctc tct ggt att tac aga gac gtt tct tta cta aaa ttg    986
Gln Trp Trp Leu Ser Gly Ile Tyr Arg Asp Val Ser Leu Leu Lys Leu
        190                 195                 200 cct aag aag gcc cat att gaa gac gtt agg gtc act aca act ttt gtg   1034
Pro Lys Lys Ala His Ile Glu Asp Val Arg Val Thr Thr Thr Phe Val
    205                 210                 215 gac tct cag tat cag gat gca gag ctt tct gtg aaa gtt gat gtc cag   1082
Asp Ser Gln Tyr Gln Asp Ala Glu Leu Ser Val Lys Val Asp Val Gln
220                 225                 230                 235 ggt tct tct tat gat cac atc aat ttc aca ctt tac gaa cct gaa gat   1130
Gly Ser Ser Tyr Asp His Ile Asn Phe Thr Leu Tyr Glu Pro Glu Asp
                240                 245                 250 gga tct aaa gtt tac gat gca agc tct ttg ttg aac gag gag aat ggg   1178
Gly Ser Lys Val Tyr Asp Ala Ser Ser Leu Leu Asn Glu Glu Asn Gly
            255                 260                 265 aac acg act ttt tca act aaa gaa ttt att tcc ttc tcc acc aaa aag   1226
Asn Thr Thr Phe Ser Thr Lys Glu Phe Ile Ser Phe Ser Thr Lys Lys
        270                 275                 280 aac gaa gaa aca gct ttc aag atc aac gtc aag gcc cca gaa cat tgg   1274
Asn Glu Glu Thr Ala Phe Lys Ile Asn Val Lys Ala Pro Glu His Trp
    285                 290                 295 acc gca gaa aat cct act ttg tac aag tac cag ttg gat tta att gga   1322
Thr Ala Glu Asn Pro Thr Leu Tyr Lys Tyr Gln Leu Asp Leu Ile Gly
300                 305                 310                 315 tct gat ggc agt gtg att caa tct att aag cac cat gtt ggt ttc aga   1370
Ser Asp Gly Ser Val Ile Gln Ser Ile Lys His His Val Gly Phe Arg
                320                 325                 330 caa gtg gag ttg aag gac ggt aac att act gtt aat ggc aaa gac att   1418
Gln Val Glu Leu Lys Asp Gly Asn Ile Thr Val Asn Gly Lys Asp Ile
            335                 340                 345 ctc ttt aga ggt gtc aac aga cat gat cac cat cca agg ttc ggt aga   1466
Leu Phe Arg Gly Val Asn Arg His Asp His His Pro Arg Phe Gly Arg
        350                 355                 360 gct gtg cca tta gat ttt gtt gtt agg gac ttg att cta atg aag aag   1514
Ala Val Pro Leu Asp Phe Val Val Arg Asp Leu Ile Leu Met Lys Lys
    365                 370                 375 ttt aac atc aat gct gtt cgt aac tcg cat tat cca aac cat cct aag   1562
Phe Asn Ile Asn Ala Val Arg Asn Ser His Tyr Pro Asn His Pro Lys
380                 385                 390                 395 gtg tat gac ctc ttc gat aag ctg ggc ttc tgg gtc att gac gag gca   1610
Val Tyr Asp Leu Phe Asp Lys Leu Gly Phe Trp Val Ile Asp Glu Ala
                400                 405                 410 gat ctt gaa act cat ggt gtt caa gag cca ttt aat cgt cat acg aac   1658
Asp Leu Glu Thr His Gly Val Gln Glu Pro Phe Asn Arg His Thr Asn
            415                 420                 425 ttg gag gct gaa tat cca gat act aaa aat aaa ctc tac gat gtt aat   1706
Leu Glu Ala Glu Tyr Pro Asp Thr Lys Asn Lys Leu Tyr Asp Val Asn
        430                 435                 440 gcc cat tac tta tca gat aat cca gag tac gag gtc gcg tac tta gac   1754
Ala His Tyr Leu Ser Asp Asn Pro Glu Tyr Glu Val Ala Tyr Leu Asp
```

-continued

| | | | | | |
|---|---|---|---|---|---|
| | 445 | | 450 | | 455 |
| aga gct tcc caa ctt gtc cta aga gat gtc aat cat cct tcg att att<br>Arg Ala Ser Gln Leu Val Leu Arg Asp Val Asn His Pro Ser Ile Ile<br>460 465 470 475 | | | | | 1802 |
| atc tgg tcc ttg ggt aac gaa gct tgt tat ggc aga aac cac aaa gcc<br>Ile Trp Ser Leu Gly Asn Glu Ala Cys Tyr Gly Arg Asn His Lys Ala<br>480 485 490 | | | | | 1850 |
| atg tac aag tta att aaa caa ttg gat cct acc aga ctt gtg cat tat<br>Met Tyr Lys Leu Ile Lys Gln Leu Asp Pro Thr Arg Leu Val His Tyr<br>495 500 505 | | | | | 1898 |
| gag ggt gac ttg aac gct ttg agt gca gat atc ttt agt ttc atg tac<br>Glu Gly Asp Leu Asn Ala Leu Ser Ala Asp Ile Phe Ser Phe Met Tyr<br>510 515 520 | | | | | 1946 |
| cca aca ttt gaa att atg gaa agg tgg agg aag aac cac act gat gaa<br>Pro Thr Phe Glu Ile Met Glu Arg Trp Arg Lys Asn His Thr Asp Glu<br>525 530 535 | | | | | 1994 |
| aat ggt aag ttt gaa aag cct ttg atc ttg tgt gag tac ggc cat gca<br>Asn Gly Lys Phe Glu Lys Pro Leu Ile Leu Cys Glu Tyr Gly His Ala<br>540 545 550 555 | | | | | 2042 |
| atg ggt aac ggt cct ggc tct ttg aaa gaa tat caa gag ttg ttc tac<br>Met Gly Asn Gly Pro Gly Ser Leu Lys Glu Tyr Gln Glu Leu Phe Tyr<br>560 565 570 | | | | | 2090 |
| aag gag aag ttt tac caa ggt ggc ttt atc tgg gaa tgg gca aat cac<br>Lys Glu Lys Phe Tyr Gln Gly Gly Phe Ile Trp Glu Trp Ala Asn His<br>575 580 585 | | | | | 2138 |
| ggt att gaa ttc gaa gat gtt agt act gca gat ggt aag ttg cat aaa<br>Gly Ile Glu Phe Glu Asp Val Ser Thr Ala Asp Gly Lys Leu His Lys<br>590 595 600 | | | | | 2186 |
| gct tat gct tat ggt ggt gac ttt aag gaa gag gtt cat gac gga gtg<br>Ala Tyr Ala Tyr Gly Gly Asp Phe Lys Glu Glu Val His Asp Gly Val<br>605 610 615 | | | | | 2234 |
| ttc atc atg gat ggt ttg tgt aac agt gag cat aat cct act ccg ggc<br>Phe Ile Met Asp Gly Leu Cys Asn Ser Glu His Asn Pro Thr Pro Gly<br>620 625 630 635 | | | | | 2282 |
| ctt gta gag tat aag aag gtt att gaa ccc gtt cat att aaa att gcg<br>Leu Val Glu Tyr Lys Lys Val Ile Glu Pro Val His Ile Lys Ile Ala<br>640 645 650 | | | | | 2330 |
| cac gga tct gta aca atc aca aat aag cac gac ttc att acg aca gac<br>His Gly Ser Val Thr Ile Thr Asn Lys His Asp Phe Ile Thr Thr Asp<br>655 660 665 | | | | | 2378 |
| cac tta ttg ttt atc gac aag gac acg gga aag aca atc gac gtt cca<br>His Leu Leu Phe Ile Asp Lys Asp Thr Gly Lys Thr Ile Asp Val Pro<br>670 675 680 | | | | | 2426 |
| tct tta aag cca gaa gaa tct gtt act att cct tct gat aca act tat<br>Ser Leu Lys Pro Glu Glu Ser Val Thr Ile Pro Ser Asp Thr Thr Tyr<br>685 690 695 | | | | | 2474 |
| gtt gtt gcc gtg ttg aaa gat gat gct ggt gtt cta aag gca ggt cat<br>Val Val Ala Val Leu Lys Asp Asp Ala Gly Val Leu Lys Ala Gly His<br>700 705 710 715 | | | | | 2522 |
| gaa att gcc tgg ggc caa gct gaa ctt cca ttg aag gta ccc gat ttt<br>Glu Ile Ala Trp Gly Gln Ala Glu Leu Pro Leu Lys Val Pro Asp Phe<br>720 725 730 | | | | | 2570 |
| gtt aca gag aca gca gaa aaa gct gcg aag atc aac gac ggt aaa cgt<br>Val Thr Glu Thr Ala Glu Lys Ala Ala Lys Ile Asn Asp Gly Lys Arg<br>735 740 745 | | | | | 2618 |
| tat gtc tca gtt gaa tcc agt gga ttg cat ttt atc ttg gac aaa ttg<br>Tyr Val Ser Val Glu Ser Ser Gly Leu His Phe Ile Leu Asp Lys Leu<br>750 755 760 | | | | | 2666 |
| ttg ggt aaa att gaa agc cta aag gtc aag ggt aag gaa att tcc agc | | | | | 2714 |

```
                Leu Gly Lys Ile Glu Ser Leu Lys Val Lys Gly Lys Glu Ile Ser Ser
                765                 770                 775 aag ttt gag ggt tct tca atc act ttc tgg aga cct cca acg aat aat                 2762
Lys Phe Glu Gly Ser Ser Ile Thr Phe Trp Arg Pro Pro Thr Asn Asn
780                 785                 790                 795 gat gaa cct agg gac ttt aag aac tgg aag aag tac aat att gat tta                 2810
Asp Glu Pro Arg Asp Phe Lys Asn Trp Lys Lys Tyr Asn Ile Asp Leu
                800                 805                 810 atg aag caa aac atc cat gga gtg agt gtc gaa aaa ggt tct aat ggt                 2858
Met Lys Gln Asn Ile His Gly Val Ser Val Glu Lys Gly Ser Asn Gly
                815                 820                 825 tct cta gct gta gtc acg gtt aac tct cgt ata tcc cca gtt gta ttt                 2906
Ser Leu Ala Val Val Thr Val Asn Ser Arg Ile Ser Pro Val Val Phe
                830                 835                 840 tac tat ggg ttt gag act gtt cag aag tac acg atc ttt gct aac aaa                 2954
Tyr Tyr Gly Phe Glu Thr Val Gln Lys Tyr Thr Ile Phe Ala Asn Lys
                845                 850                 855 ata aac ttg aac act tct atg aag ctt act ggc gaa tat cag cct cct                 3002
Ile Asn Leu Asn Thr Ser Met Lys Leu Thr Gly Glu Tyr Gln Pro Pro
860                 865                 870                 875 gat ttc cca aga gtt ggg tac gaa ttc tgg cta gga gat agt tat gaa                 3050
Asp Phe Pro Arg Val Gly Tyr Glu Phe Trp Leu Gly Asp Ser Tyr Glu
                880                 885                 890 tca ttt gaa tgg tta ggt cgc ggg ccc ggc gaa tca tat ccg gat aag                 3098
Ser Phe Glu Trp Leu Gly Arg Gly Pro Gly Glu Ser Tyr Pro Asp Lys
                895                 900                 905 aag gaa tct caa aga ttc ggt ctt tac gat tcc aaa gat gta gag gaa                 3146
Lys Glu Ser Gln Arg Phe Gly Leu Tyr Asp Ser Lys Asp Val Glu Glu
                910                 915                 920 ttc gta tat gac tat cct caa gaa aat gga aat cat aca gat acc cac                 3194
Phe Val Tyr Asp Tyr Pro Gln Glu Asn Gly Asn His Thr Asp Thr His
925                 930                 935 ttt ttg aac atc aaa ttt gaa ggt gca gga aaa cta tcg atc ttc caa                 3242
Phe Leu Asn Ile Lys Phe Glu Gly Ala Gly Lys Leu Ser Ile Phe Gln
940                 945                 950                 955 aag gag aag cca ttt aac ttc aag att tca gac gaa tac ggg gtt gat                 3290
Lys Glu Lys Pro Phe Asn Phe Lys Ile Ser Asp Glu Tyr Gly Val Asp
                960                 965                 970 gaa gct gcc cac gct tgt gac gtt aaa aga tac ggc aga cac tat cta                 3338
Glu Ala Ala His Ala Cys Asp Val Lys Arg Tyr Gly Arg His Tyr Leu
                975                 980                 985 agg ttg gac cat gca atc cat ggt gtt ggt agc gaa gca tgc gga cct                 3386
Arg Leu Asp His Ala Ile His Gly Val Gly Ser Glu Ala Cys Gly Pro
                990                 995                 1000 gct gtt ctg gac cag tac aga ttg aaa gct caa gat ttc aac ttt              3431
Ala Val Leu Asp Gln Tyr Arg Leu Lys Ala Gln Asp Phe Asn Phe
                1005                1010                1015 gag ttt gat ctc gct ttt gaa gac tac aag gat gac gat gac aag                  3476
Glu Phe Asp Leu Ala Phe Glu Asp Tyr Lys Asp Asp Asp Asp Lys
                1020                1025                1030 taa                                                                           3479

<210> SEQ ID NO 2
<211> LENGTH: 1033
<212> TYPE: PRT
<213> ORGANISM: Artificial Sequence
<220> FEATURE:
<223> OTHER INFORMATION: Synthetic Construct

<400> SEQUENCE: 2
```

```
Met Ser Cys Leu Ile Pro Glu Asn Leu Arg Asn Pro Lys Lys Val His
1               5                   10                  15
Glu Asn Arg Leu Pro Thr Arg Ala Tyr Tyr Asp Gln Asp Ile Phe
            20                  25                  30
Glu Ser Leu Asn Gly Pro Trp Ala Phe Ala Leu Phe Asp Ala Pro Leu
                35                  40                  45
Asp Ala Pro Asp Ala Lys Asn Leu Asp Trp Glu Thr Ala Lys Lys Trp
        50                  55                  60
Ser Thr Ile Ser Val Pro Ser His Trp Glu Leu Gln Glu Asp Trp Lys
65                  70                  75                  80
Tyr Gly Lys Pro Ile Tyr Thr Asn Val Gln Tyr Pro Ile Pro Ile Asp
                    85                  90                  95
Ile Pro Asn Pro Pro Thr Val Asn Pro Thr Gly Val Tyr Ala Arg Thr
                100                 105                 110
Phe Glu Leu Asp Ser Lys Ser Ile Glu Ser Phe Glu His Arg Leu Arg
            115                 120                 125
Phe Glu Gly Val Asp Asn Cys Tyr Glu Leu Tyr Val Asn Gly Gln Tyr
        130                 135                 140
Val Gly Phe Asn Lys Gly Ser Arg Asn Gly Ala Glu Phe Asp Ile Gln
145                 150                 155                 160
Lys Tyr Val Ser Glu Gly Glu Asn Leu Val Val Lys Val Phe Lys
                    165                 170                 175
Trp Ser Asp Ser Thr Tyr Ile Glu Asp Gln Asp Gln Trp Trp Leu Ser
                180                 185                 190
Gly Ile Tyr Arg Asp Val Ser Leu Leu Lys Leu Pro Lys Lys Ala His
            195                 200                 205
Ile Glu Asp Val Arg Val Thr Thr Thr Phe Val Asp Ser Gln Tyr Gln
        210                 215                 220
Asp Ala Glu Leu Ser Val Lys Val Asp Val Gln Gly Ser Ser Tyr Asp
225                 230                 235                 240
His Ile Asn Phe Thr Leu Tyr Glu Pro Glu Asp Gly Ser Lys Val Tyr
                    245                 250                 255
Asp Ala Ser Ser Leu Leu Asn Glu Glu Asn Gly Asn Thr Thr Phe Ser
                260                 265                 270
Thr Lys Glu Phe Ile Ser Phe Ser Thr Lys Lys Asn Glu Glu Thr Ala
            275                 280                 285
Phe Lys Ile Asn Val Lys Ala Pro Glu His Trp Thr Ala Glu Asn Pro
        290                 295                 300
Thr Leu Tyr Lys Tyr Gln Leu Asp Leu Ile Gly Ser Asp Gly Ser Val
305                 310                 315                 320
Ile Gln Ser Ile Lys His His Val Gly Phe Arg Gln Val Glu Leu Lys
                    325                 330                 335
Asp Gly Asn Ile Thr Val Asn Gly Lys Asp Ile Leu Phe Arg Gly Val
                340                 345                 350
Asn Arg His Asp His His Pro Arg Phe Gly Arg Ala Val Pro Leu Asp
            355                 360                 365
Phe Val Val Arg Asp Leu Ile Leu Met Lys Lys Phe Asn Ile Asn Ala
        370                 375                 380
Val Arg Asn Ser His Tyr Pro Asn His Pro Lys Val Tyr Asp Leu Phe
385                 390                 395                 400
Asp Lys Leu Gly Phe Trp Val Ile Asp Glu Ala Asp Leu Glu Thr His
                    405                 410                 415
Gly Val Gln Glu Pro Phe Asn Arg His Thr Asn Leu Glu Ala Glu Tyr
```

```
            420                 425                 430
Pro Asp Thr Lys Asn Lys Leu Tyr Asp Val Asn Ala His Tyr Leu Ser
            435                 440                 445
Asp Asn Pro Glu Tyr Glu Val Ala Tyr Leu Asp Arg Ala Ser Gln Leu
            450                 455                 460
Val Leu Arg Asp Val Asn His Pro Ser Ile Ile Ile Trp Ser Leu Gly
465                 470                 475                 480
Asn Glu Ala Cys Tyr Gly Arg Asn His Lys Ala Met Tyr Lys Leu Ile
            485                 490                 495
Lys Gln Leu Asp Pro Thr Arg Leu Val His Tyr Glu Gly Asp Leu Asn
            500                 505                 510
Ala Leu Ser Ala Asp Ile Phe Ser Phe Met Tyr Pro Thr Phe Glu Ile
            515                 520                 525
Met Glu Arg Trp Arg Lys Asn His Thr Asp Glu Asn Gly Lys Phe Glu
            530                 535                 540
Lys Pro Leu Ile Leu Cys Glu Tyr Gly His Ala Met Gly Asn Gly Pro
545                 550                 555                 560
Gly Ser Leu Lys Glu Tyr Gln Glu Leu Phe Tyr Lys Glu Lys Phe Tyr
            565                 570                 575
Gln Gly Gly Phe Ile Trp Glu Trp Ala Asn His Gly Ile Glu Phe Glu
            580                 585                 590
Asp Val Ser Thr Ala Asp Gly Lys Leu His Lys Ala Tyr Ala Tyr Gly
            595                 600                 605
Gly Asp Phe Lys Glu Glu Val His Asp Gly Val Phe Ile Met Asp Gly
            610                 615                 620
Leu Cys Asn Ser Glu His Asn Pro Thr Pro Gly Leu Val Glu Tyr Lys
625                 630                 635                 640
Lys Val Ile Glu Pro Val His Ile Lys Ile Ala His Gly Ser Val Thr
            645                 650                 655
Ile Thr Asn Lys His Asp Phe Ile Thr Thr Asp His Leu Leu Phe Ile
            660                 665                 670
Asp Lys Asp Thr Gly Lys Thr Ile Asp Val Pro Ser Leu Lys Pro Glu
            675                 680                 685
Glu Ser Val Thr Ile Pro Ser Asp Thr Thr Tyr Val Val Ala Val Leu
            690                 695                 700
Lys Asp Asp Ala Gly Val Leu Lys Ala Gly His Glu Ile Ala Trp Gly
705                 710                 715                 720
Gln Ala Glu Leu Pro Leu Lys Val Pro Asp Phe Val Thr Glu Thr Ala
            725                 730                 735
Glu Lys Ala Ala Lys Ile Asn Asp Gly Lys Arg Tyr Val Ser Val Glu
            740                 745                 750
Ser Ser Gly Leu His Phe Ile Leu Asp Lys Leu Leu Gly Lys Ile Glu
            755                 760                 765
Ser Leu Lys Val Lys Gly Lys Glu Ile Ser Ser Lys Phe Glu Gly Ser
            770                 775                 780
Ser Ile Thr Phe Trp Arg Pro Pro Thr Asn Asn Asp Glu Pro Arg Asp
785                 790                 795                 800
Phe Lys Asn Trp Lys Lys Tyr Asn Ile Asp Leu Met Lys Gln Asn Ile
            805                 810                 815
His Gly Val Ser Val Glu Lys Gly Ser Asn Gly Ser Leu Ala Val Val
            820                 825                 830
Thr Val Asn Ser Arg Ile Ser Pro Val Val Phe Tyr Tyr Gly Phe Glu
            835                 840                 845
```

```
Thr Val Gln Lys Tyr Thr Ile Phe Ala Asn Lys Ile Asn Leu Asn Thr
    850                 855                 860

Ser Met Lys Leu Thr Gly Glu Tyr Gln Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
                900                 905                 910

Phe Gly Leu Tyr Asp Ser Lys Asp Val Glu Glu Phe Val Tyr Asp Tyr
                915                 920                 925

Pro Gln Glu Asn Gly Asn His Thr Asp Thr His Phe Leu Asn Ile Lys
    930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
                980                 985                 990

Ile His Gly Val Gly Ser Glu Ala  Cys Gly Pro Ala Val  Leu Asp Gln
                995                 1000                1005

Tyr Arg  Leu Lys Ala Gln Asp  Phe Asn Phe Glu Phe  Asp Leu Ala
    1010                1015                1020

Phe Glu  Asp Tyr Lys Asp Asp  Asp Asp Lys
    1025                1030

<210> SEQ ID NO 3
<211> LENGTH: 580
<212> TYPE: DNA
<213> ORGANISM: Artificial Sequence
<220> FEATURE:
<223> OTHER INFORMATION: Kluyveromyces lactis beta-galactosidase
      promoter region 1

<400> SEQUENCE: 3
cgggagtcag tgggccgaaa tatgttcttg gcctagaact taatctggtt tgatcatgcc      60
aatacttgcc tgagtgcccg acttttttgcc caccctcttg ccttctgtca tccttcaaaa    120
cccacctgtt ttccagccgt atcttcgctc gcatctacac atactgtgcc atatcttgtg    180
tgtagccgga cgtgactatg accaaaaaca aacaaggaga actgttcgcc gatttgtaac    240
actcctgcat ccatccaagt gggtatgcgc tatgcaatgt taagctaggt caggtcagac    300
caggtccaag gacagcaact tgactgtatg caacctttac catctttgca cagaacatac    360
ttgtagctag ctagttacac ttatggaccg aaaaggcacc ccaccatgtc tgtccggctt    420
tagagtacgg ccgcagaccg ctgatttgcc ttgccaagca gtagtcacaa tgcatcgcat    480
gagcacacgg gcacgggcac gggcacagga accattggca aaaataccag atacactata    540
ccgacgtata tcaagcccaa gtttaaaatt cctaaatttc                          580

<210> SEQ ID NO 4
<211> LENGTH: 1632
<212> TYPE: DNA
<213> ORGANISM: Artificial Sequence
<220> FEATURE:
<223> OTHER INFORMATION: Kluyveromyces lactis beta-galactosidase
      promoter region 2

<400> SEQUENCE: 4
```

```
cgcgggatc gactcataaa atagtaacct tctaatgcgt atctattgac taccaaccat    60
tagtgtggtt gcagaaggcg gaattctccc ttcttcgaat tcagcttgct ttttcatttt   120
ttattttcca tttttcagtt tttgtttgtg tcgaatttag ccagttgctt ctccaagatg   180
aaaaaaccc ctgcgcagtt tctgtgctgc aagatcctaa tcgacttttc cacccccac    240
aaaagtaaat gttctttttgt tacattcgcg tgggtagcta gctccccgaa tcttcaaagg   300
acttagggac tgcactacat cagagtgtgt tcacctggtt tgctgcctgg tttgaaagaa   360
aagagcaggg aactcgcggg ttcccggcga ataatcatgc gatagtcctt tggccttcca   420
agtcgcatgt agagtagaca acagacaggg agggcaggaa ggatctttca ctgagatcct   480
gtatcttgtt gggtaagtcg gatgaaaggg gaatcgtatg agattggaga ggatgcggaa   540
gaggtaacgc cttttgttaa cttgtttaat tattatgggg caggcgagag ggggaggaat   600
gtatgtgtgt gaggcgggcg agacggagcc atccaggcca ggtagaaata gagaaagccg   660
aatgttagac aatatggcag cgtagtagag taggtaggta ggcaagtact gctagcaaag   720
aggagaaggg taagctcact cttcgcattc cacaccgtta gtgtgtcagt ttgaacaaaa   780
aaacaatcat cataccaatt gatggactgt ggactggctt ttggaacggc ttttcggact   840
gcgattattc gtgaggaatc aaggtaggaa tttggtcata tttacggaca acagtgggtg   900
attcccatat ggagtaggaa aacgagatca tggtatcctc agatatgttg cggaattctg   960
ttcaccgcaa agttcagggt gctctggtgg gtttcggttg gtctttgctt tgcttctccc  1020
ttgtcttgca tgttaataat agcctagcct gtgagccgaa acttagggta ggcttagtgt  1080
tggaacgtac atatgtatca cgttgacttg gtttaaccag cgacctggt agccagccat   1140
acccacacac gttttttgta tcttcagtat agttgtgaaa agtgtagcgg aaatttgtgg  1200
tccgagcaac agcgtctttt tctagtagtg cggtcggtta cttggttgac attggtattt  1260
ggactttgtt gctacaccat tcactacttg aagtcgagtg tgaagggtat gatttctagt  1320
ggtgaacacc tttagttacg taatgttttc attgctgttt tacttgagat ttcgattgag  1380
aaaaaggtat ttaatagctc gaatcaatgt gagaacagag agaagatgtt cttccctaac  1440
tcgaaaggta tatgaggctt gtgtttctta ggagaattat tattcttttg ttatgttgcg  1500
cttgtagttg gaaaaggtga agagacaaaa gctggaattg tgagcggata acaagctcaa  1560
cacttgaaat ttaggaaaga gcagaatttg gcaaaaaaaa taaaaaaaaa ataaacacac  1620
atactcatcg ag                                                      1632
```

```
<210> SEQ ID NO 5
<211> LENGTH: 582
<212> TYPE: DNA
<213> ORGANISM: Artificial Sequence
<220> FEATURE:
<223> OTHER INFORMATION: Kluyveromyces lactis beta-galactosidase
      terminator

<400> SEQUENCE: 5
```

```
ttatacttag ataagtatgt acttacaggt atatttctat gagatactga tgtatacatg    60
catgataata tttaaacggt tattagtgcc gattgtcttg tgcgataatg acgttcctat   120
caaagcaata cacttaccac ctattacatg ggccaagaaa atattttcga acttgtttag   180
aatattagca cagagtatat gatgatatcc gttagattat gcatgattca ttcctacaac   240
tttttcgtag cataaggatt aattacttgg atgccaataa aaaaaaaaa catcgagaaa   300
atttcagcat gctcagaaac aattgcagtg tatcaaagta aaaaaaagat tttcactaca   360
```

-continued

```
tgttcctttt gaagaaagaa aatcatggaa cattagattt acaaaaattt aaccaccgct    420
gattaacgat tagaccgtta agcgcacaac aggttattag tacagagaaa gcattctgtg    480
gtgttgcccc ggactttctt ttgcgacata ggtaaatcga ataccatcat actatctttt   540
ccaatgactc cctaaagaaa gactcttctt cgatgttgta ta                       582
```

KLUYVEROMYCES LACTIS YEAST STRAIN AND METHODS FOR THE PRODUCTION OF SUGARS, ETHANOL, BETA-GALACTOSIDASE AND BIOMASS

CROSS REFERENCE TO RELATED APPLICATION

This Application is a 371 of PCT/ES2011/070550 filed on Jul. 27, 2011, which claims the priority of Spanish Patent Application No, 201131065 filed on Jun. 24, 2011, both applications are incorporated herein by reference in their entirety.

FIELD OF THE INVENTION

The present invention is related to a *Kluyveromyces lactis* yeast strain modified by means of genomic integration capable of secreting β-galactosidase into the medium. Said yeast strain is used in methods for the production of sugars, biomass, ethanol and β-galactosidase in lactose-containing media, such as milk or whey.

BACKGROUND OF THE INVENTION

Whey is the liquid remaining after the precipitation and separation of casein from milk during cheese elaboration. This whey retains 55% of the nutrients in milk (it is 85-90% of the milk volume) and has high biological and chemical oxygen demand so it is considered a contaminating by-product, and an environmental problem important for dairies.

Until now no technology has been developed that has proven to be sufficiently profitable for processing large volumes of whey. The main drawback is the small number of microorganisms capable of growing in the milk whey. The wild strains of respiring yeasts, such as *Kluyveromyces lactis*, are unable to achieve alcohol concentrations sufficient to recoup the investment.

The problem posed by the art is to provide a *Kluyveromyces lactis* strain capable of natively and actively secreting β-galactosidase into the medium capable of achieving alcohol concentrations higher than the wild strain. The solution proposed by the present invention is a *Kluyveromyces lactis* yeast strain deposited in the Deutsche Sammlung von Mikroorganismen und Zellkulturen GmbH (DSMZ) Culture Collection with deposit number DSM 24900, comprising the sequence identified by SEQ ID NO: 1.

DESCRIPTION OF THE INVENTION

The present invention is a *Kluyveromyces lactis* yeast strain deposited in the Deutsche Sammlung von Mikroorganismen und Zellkulturen GmbH (DSMZ) Culture Collection with deposit number DSM 24900, comprising the sequence identified by SEQ ID NO: 1.

The *Kluyveromyces lactis* yeast strain of the invention, was deposited on Jun. 6, 2011, under the provisions of the Budapest Treaty, in the Deutsche Sammlung von Mikroorganismen and Zellkulturen GmbH (DSMZ) Culture Collection in Inhoffenstraβe 7 B, 38124 Braunschweig (Germany), by the depositor Queizuar, SL, A Silva-Bama, s/n, 15822 Touro, A Coruna (Spain).

The Kluyveromyces lactis yeast strain received the deposit number DSM 24900 after the Deposit International Authority found that the strain was viable. All restrictions to the deposited material will be irrevocably removed upon issuance of the patent application.

The strain of the invention comprises a DNA construct identified by SEQ ID NO: 1, comprising a signal sequence of the preprofactor α of *Kluyveromyces lactis* fused in the same reading frame with the mature form of the β-galactosidase of *Kluyveromyces lactis*. The signal sequence of the preprofactor α of *Kluyveromyces lactis* is able to promote the secretion of the β-galactosidase of the strain of the invention. It has been surprisingly found that, the yeast strain containing said construction, although it has levels of growth lower than those of the native strain, secrets β-galactosidase into the medium in its active form with yields up to 113% higher than the same *K. lactis* strain without modification. The strain can be used for the production of sugars, biomass, ethanol and β-galactosidase from a lactose-rich culture medium.

The construction identified by SEQ ID NO: 1 also comprises the coding sequence for the FLAG peptide, recognized by a monoclonal antibody and which can serve to recognize the resulting fusion protein by immunoaffinity chromatography. Said sequence can be substituted by sequences encoding tag peptides with an equivalent function such as c-myc, HA, E. It can also be substituted by peptide sequences which allow the isolation or purification of the peptide or fusion protein, for example, a polyhistidine sequence.

Preferably, the tag peptide is the FLAG epitope, and is linked to the C-terminus of the β-galactosidase.

One embodiment is a strain of the invention further comprising the sequences identified by SEQ ID NO: 3, 4 and 5.

This strain comprises a promoter for the expression of the protein. Said promoter is the promoter of the LAC4 gene, which is the sequence identified by SEQ ID NO: 3 and 4. Said strain also comprises a transcriptional terminator. Said transcriptional terminator is the terminator of the LAC4 gene, which is identified by SEQ ID NO: 5.

Another embodiment is a strain of the invention comprising a sequence having an identity of 95% with respect to SEQ ID NO: 1. And another embodiment is that said identity is 90%.

In the present application, said percentage of identity in a certain sequence is calculated taking into account, that an identity of 95% means that 95% of residues of the complete sequence of the DNA construction identified by the sequence SEQ ID NO: 1 are identical to the residues of that certain sequence.

A preferred embodiment is a protein obtained from the strain of the invention, the amino acid sequence of which is identified by SEQ ID NO: 2.

Another embodiment is a vector comprising the sequences identified by SEQ ID NO: 1, 3, 4 and 5.

Said vector is used to introduce said sequences into the strain of the invention. There are different methods suitable for introducing a DNA molecule in the strain of the invention:

Spheroplast transformation, which involves the removal of the yeast cell wall and contacting the spheroplasts with the plasmid in the presence of PEG, Transformation with $Li^+$, which involves treating the yeast cells with monovalent alkali cations ($Na^+$, $K^+$, $Rb^+$, $Cs^+$ and $Li^+$) in combination with PEG to stimulate the uptake of DNA by the intact cells.

Electroporation, which involves the administration of electrical pulses to yeast resulting in the opening of pores in the membrane of spheroplasts and intact yeast cells.

The strains of the invention are capable of growing in a lactose-rich medium, which is degraded forming glucose and galactose. Such that an embodiment of the invention is a method for the obtainment of sugars, wherein a *Kluyveromyces lactis* yeast strain comprising the sequence identified by SEQ ID NO: 1 is cultured in the presence of lactose-containing medium. A preferred embodiment is the method for the obtainment of sugar of the invention wherein said lactose-containing medium is selected from the group consisting of milk, whey, whey resulting from the preparation of butter, whey resulting after casein precipitation, milk permeate, whey permeate, acid whey and YPL culture medium.

A preferred embodiment is a method for the obtainment of sugars of the invention, wherein said sugar is glucose and/or galactose.

Another preferred embodiment is a method for the obtainment of sugars of the invention, wherein said yeast strain comprises a sequence that has an identity of 95% with respect to SEQ ID NO: 1. In another more preferred embodiment, said identity is 90%.

In the method for the obtainment of sugars, the cell respiration of the strain of the invention is forced by means of high stirring and aeration, thereby avoiding yield losses by fermentation of the sugars to ethanol.

The lactose-containing media that can be used as carbon source in the context of the present invention include both synthetic media and natural products and derivatives thereof. Synthetic or semi-synthetic media that can be used in the context of the present invention include YPL, containing 1% yeast extract, 2% bactopeptone, and an amount of lactose that varies between 0.5% and 6%.

Lactose-rich natural products that can be used as a culture medium for the strain of the invention include milk and derivatives thereof, such as skim milk, the whey resulting from the preparation of butter (buttermilk), the whey resulting after casein precipitation or the permeate of a milk product which can be a milk permeate or a whey permeate. The present invention contemplates the use of milk of virtually any origin, including, without limitation, cow, human, goat, sheep, camel, and buffalo milk and the like. Preferably, the milk is subjected to treatment with rennet of animal origin (extract obtained from the abomasums of the stomach of ruminants), plant origin or recombinant at temperatures between 30 and 40° C., which results in the coagulation of milk casein, which carries most of the fat fraction of the same. After the elimination of the clot, the whey is obtained, which can be used as such (the so-called "sweet whey") or it may be subjected to an additional deproteinization process, for example, by ultrafiltration or other separation techniques based on porous membranes with a separation limit of 17-20 kDa. Likewise, the invention contemplates the use of the so-called acid whey, resulting from the precipitation of milk proteins in acid medium.

The whey can be concentrated by aerosol spraying to result in fractions with a higher content of dry solid matter than the original whey, including a solid product called whey permeate. Typical contents in dry solid matter range from 5 to 6% in the whey, through values above 30%, particularly between 50 and 60% of the concentrates. The lactose concentration varies between 70 and 75% of total dry solid matter in the case of sweet whey and reaches values between 82 and 86% in the case of whey permeates.

Glucose and galactose which are formed as a result of the hydrolysis of lactose may be recovered from the culture medium using techniques well known by the person skilled in the art. Preferably, glucose and galactose are purified by adsorption with activated carbon preparations with different properties or by using ceramic membranes.

The lactose in the culture medium is digested by the strains of the invention to give glucose and galactose which, in turn, are suitable substrates for alcoholic fermentation producing alcohols. So that one embodiment of the invention is a method for the obtainment of ethanol wherein a *Kluyveromyces lactis* yeast strain comprising the sequence identified by SEQ ID NO: 1 is cultured in the presence of a lactose-containing medium.

A preferred embodiment is a method for the obtainment of ethanol of the invention, wherein said lactose-containing medium is selected from the group consisting of milk, whey, whey resulting from the preparation of butter, whey resulting after casein precipitation, milk permeate, whey permeate, acid whey and YPL culture medium.

Another preferred embodiment is a method for the obtainment of ethanol of the invention, wherein said yeast strain comprises a sequence that has an identity of 95% with respect to SEQ ID NO: 1. In another more preferred embodiment, said identity is 90%.

Ethanol can be used as fuel, in beverages or at an industrial level. Normally, the alcoholic fermentation for producing ethanol is carried out for 30-60 hours, at a temperature around 32° C. The ethanol is recovered from the medium using conventional techniques, such as distillation.

The strain of the invention is able to produce and secrete β-galactosidase into the medium. So that a preferred embodiment of the invention is a method for the obtainment of the protein identified by SEQ ID NO: 2, wherein a *Kluyveromyces lactis* yeast strain comprising the sequence identified by SEQ ID NO: 1 is cultured in the presence of lactose-containing medium.

A preferred embodiment is a method for the obtainment of the protein identified by SEQ ID NO: 2 of the invention, wherein said lactose-containing medium is selected from the group consisting of milk, whey, whey resulting from the preparation of butter, whey resulting after casein precipitation, milk permeate, whey permeate, acid whey and YPL culture medium.

Another preferred embodiment is a method for the obtainment of the protein identified by the sequence SEQ ID NO: 2 of the invention, wherein said yeast strain comprises a sequence that has an identity of 95% with respect to SEQ ID NO: 1. In another more preferred embodiment, said identity is 90%.

The β-galactosidase protein can be conveniently purified in a single step of affinity chromatography using substrate analogs, such as p-amino phenyl-β-D-thiogalactopyranoside.

The purification of β-galactosidase of *K. lactis* and its variants can be carried out using methods known in the art. The determination of the degree of purity of the β-galactosidase can be estimated by the value of the specific enzyme activity which is calculated by dividing the number of units of enzyme activity by the amount of mg of protein in a given volume. Preferably, the enzyme activity is determined by the method of Guarente (Guarente, L., 1983, Methods in Enzymology, 101: 181-191).

A preferred embodiment of the invention is a method for the obtainment of biomass, wherein a *Kluyveromyces lactis* yeast strain comprising the sequence identified by SEQ ID NO: 1 is cultured in the presence of a lactose-containing medium.

A preferred embodiment is a method for the obtainment of biomass of the invention, wherein said lactose-containing medium is selected from the group consisting of milk, whey, whey resulting from the preparation of butter, whey resulting after casein precipitation, milk permeate, whey permeate, acid whey and YPL culture medium.

Another preferred embodiment is a method for the obtainment of biomass of the invention, wherein said yeast strain comprises a sequence that has an identity of 95% with respect to SEQ ID NO: 1. In another more preferred embodiment, said identity is 90%.

The biomass can be recovered from the culture medium by any technique known to those skilled in the art including, without limitation, centrifugation, deposition or filtration. Preferably, the technique used must significantly reduce the damage to the cells. In case that the same culture is used for preparation of ethanol and biomass, the separation of the biomass of the yeast cells must significantly reduce the loss of ethanol.

Normally, the yeast recovered from the culture medium is washed with an aqueous solution to remove unwanted materials that could be associated with the yeast. Preferably, the protein content in yeast is between 35 and 65%.

The yeast biomass recovered can be used as ingredient in food products without further processing. The recovered biomass can also be lysed and, optionally, the intact cells can be separated. Lysed yeast cells can be used in culture media as yeast extract or may be further processed to separate their various components, such as peptides, nucleotides, amino acids or components specific of the cell wall such as chitin, glucans, mannans and oligosaccharides.

Free Text of the Sequence Listing

In the following, the free text that appears in the sequence listing is shown.

SEQ ID NO: 1. Secretion domain of the *Kluyveromyces lactis* preprofactor α, *Kluyveromyces lactis* β-galactosidase and FLAG peptide.

SEQ ID NO: 3. Region 1 of the *Kluyveromyces lactis* β-galactosidase promoter.

SEQ ID NO: 4. Region 2 of the *Kluyveromyces lactis* β-galactosidase promoter.

SEQ ID NO: 5. *Kluyveromyces lactis* β-galactosidase terminator.

PREFERRED EMBODIMENTS

EXAMPLE 1

Construction of the Vector and Transformation of the Strain of the Invention

From the LAC4 sequence encoding the *K. lactis* β-galactosidase, oligonucleotides primers were designed in order to amplify the gene by polymerase chain reaction (PCR) with the FLAG peptide and subsequently ligate it into a yeast expression vector to obtain the corresponding plasmid.

Figure 4:
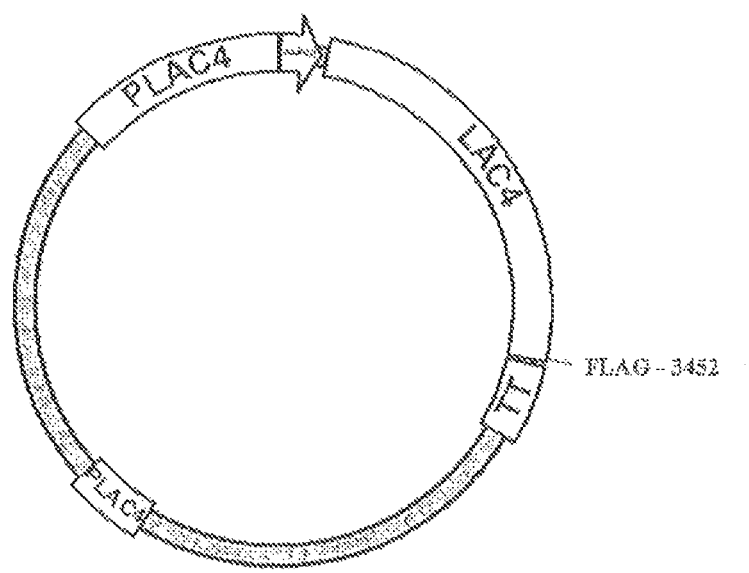
FIG. 4. It shows a schematic representation of the structure of the vector comprising SEQ ID NO: 1.

The vector contains the promoter of the *K. lactis* β-galactosidase which is induced in the presence of galactose and/or lactose, a sequence encoding the signal sequence of the yeast preprofactor α, and the terminator of the *K. lactis* β-galactosidase. The structure of the vector is represented in FIG. 4.

The gene is incorporated into the yeast in the LAC4 locus by homologous recombination. In the case of this strain, several tandem copies of the gene were integrated in the yeast genome.

The yeast strain was transformed with the resulting constructs using the lithium acetate method from Ito et al. (Ito et al., 3983, J. Bacteriol., 153: 163-168).

EXAMPLE 2

Media and Culture Conditions of the Strata of the Invention

With the recombinant strain obtained, cultures in media rich in galactose and/or lactose, as well as other carbon sources (glucose, glycerol, etc.) were carried out in flasks of different volumes (50, 100, 250, 500, 1000 and 2000 ml), trying to maintain a ratio of 1/2,5 with respect to the liquid in the flask volume. Cultures were also carried out in larger volumes (fermenters).

The cultures were carried out at the optimal temperature of the yeast, and with different degrees of stirring (50 rpm-500 rpm) to verify optimal production of biomass, protein or ethanol.

In the case of the use of whey, this was autoclaved and centrifuged to obtain a lactose-rich medium as clean as possible.

Also, the minimum and maximum concentrations of inoculum for each of the cases were tested.

EXAMPLE 3

Determination of Lactose and Ethanol Concentrations and β-Galactosidase Activity For the determination of lactose and ethanol both commercial tests from Roche and other suppliers (always following the recommendations of the Supplier) and High Resolution Liquid Chromatography were used.

The determination of the β-galactosidase activity was performed following the method of Guarente. The Enzyme Unit (EU) was defined as the amount of enzyme that releases one nmol of o-nitrophenol per minute in test conditions. The units are given as E.U./ml of culture medium or E.U./mg protein.

Figure 1:
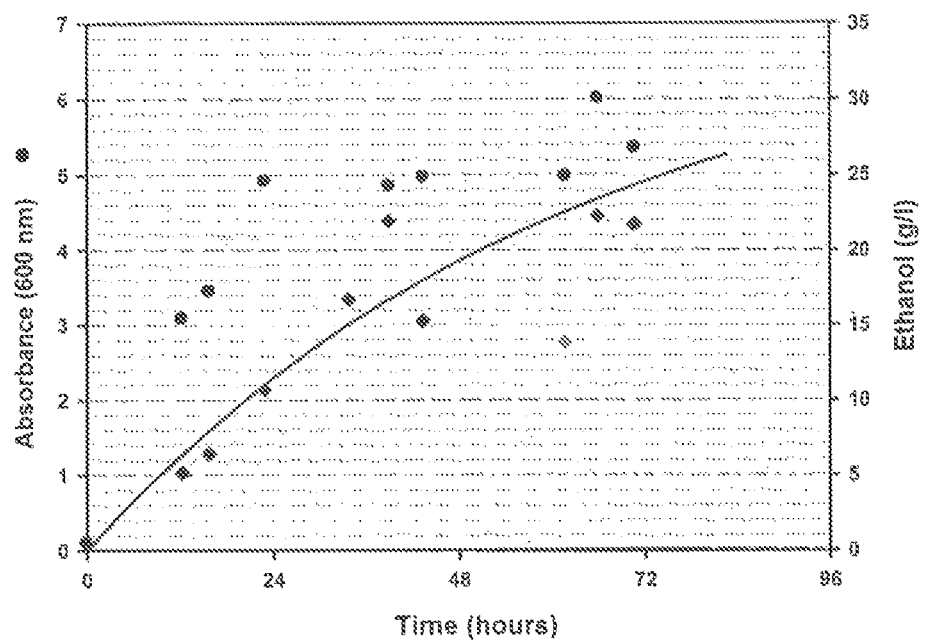
FIG. 1: Growth and ethanol production of the *Kluyveromyces lactis* strain in whey. Upper panel, growth and yield in grams of ethanol per gram of cells of the *Kluyveromyces lactis* wild strain. Lower panel, growth and yield in grams of ethanol per gram of cells of the *Kluyveromyces lactis* strain of the invention.
Figure 1:
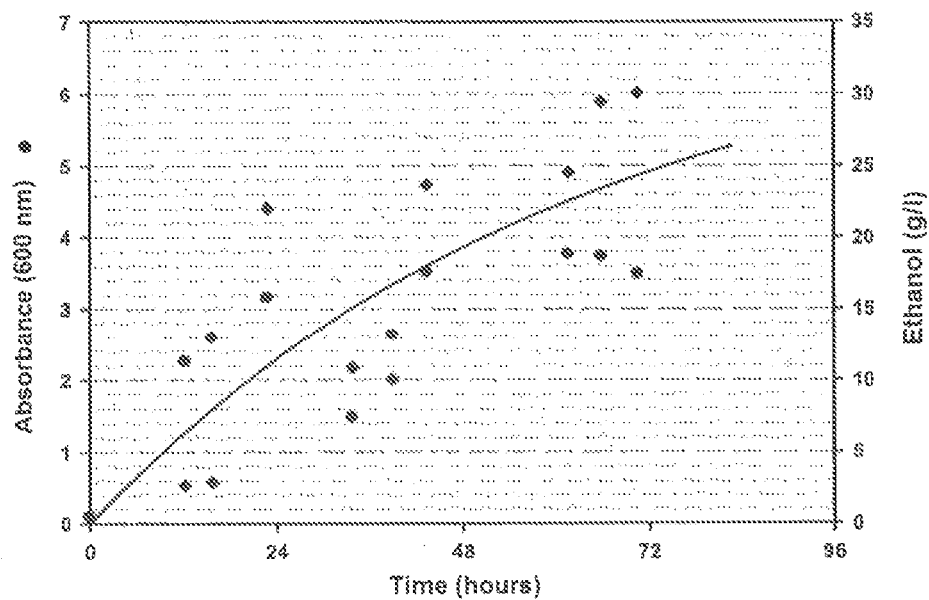

EXAMPLE 4

β-Galactosidase and Ethanol Production of the Strain of the Invention in Whey in Culture in Glass Tubes The control strain and the strain of the invention were cultured in whey in sealed glass tubes and kept at 30° C. with gentle stirring (about 50 rpm) tor the 72 hours that the experiment lasted. FIG. 1 shows the production of ethanol of the strain of the invention and of the wild strain (used as a control) over a 72 hours culture. The strain of the invention obtained 13.8 g of ethanol per gram of cells, while the control strain obtained 6.4 g of ethanol per gram of cells.

Figure 2:
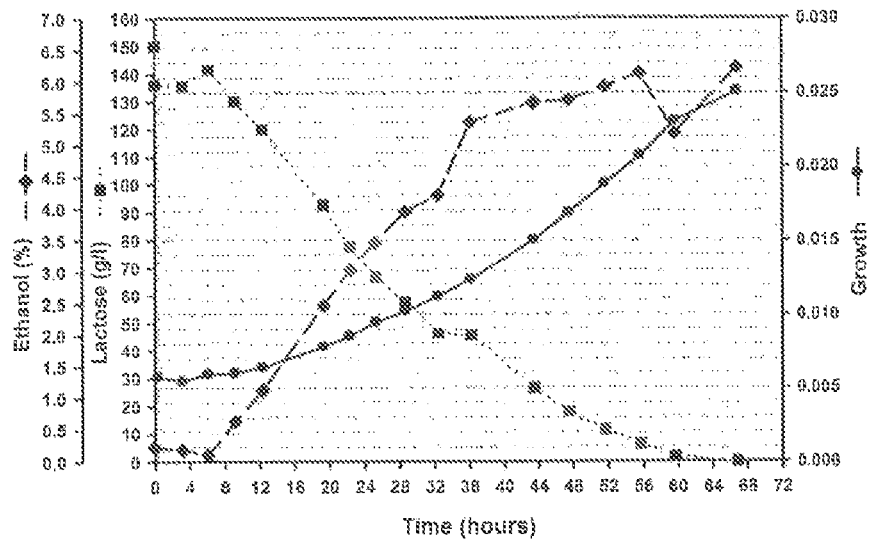
FIG. 2: Growth, lactose consumption and ethanol production of the *Kluyveromyces lactis* strain of the invention in whey in a fermenter at 30° C.

EXAMPLE 5

β-Galactosidase and Ethanol Production of the Strain of the Invention in Whey in Culture in Fermenter The strain of the invention was cultured in whey in a fermenter at 30° C. FIG. 2 shows a culture of the strain of the invention in whey, the amount of lactose consumed, the amount of ethanol produced, as well as the growth after 68 hours of culture.

Figure 3:
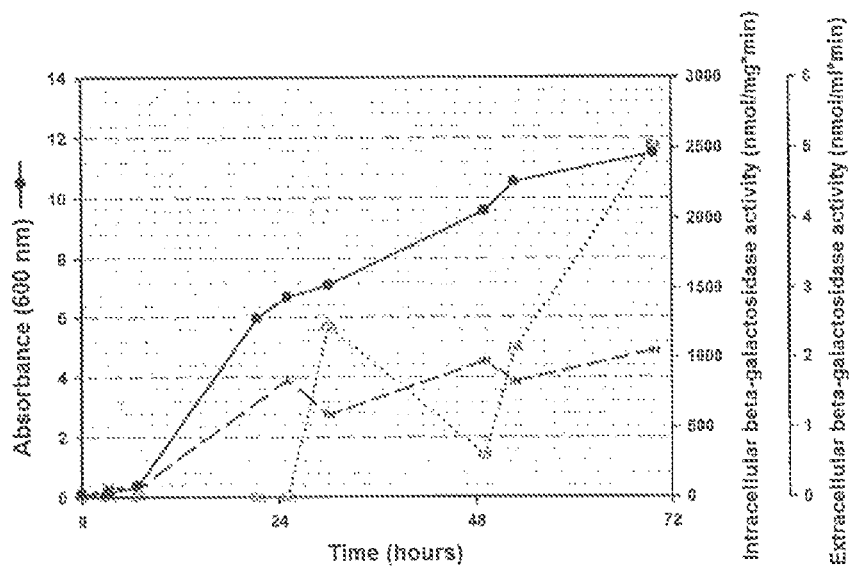
FIG. 3: Growth, intracellular and extracellular β-galactosidase activity of the *Kluyveromyces lactis* strain of the invention growing in a lactose-rich medium in 5% YPL culture medium (1% yeast extract, 0.5% bactopeptone, and 5% lactose) in flasks at 30° C. and 150 rpm stirring.

EXAMPLE 6

β-Galactosidase and Ethanol Production of the Strain of the Invention in 5% YPL Culture Medium The strain of the invention was cultured in 5% YPL culture medium (1% yeast extract, 0.5% bactopeptone, and 5% lactose) in flasks at 30° C. and 150 rpm stirring. FIG. 3 shows an example of the ability to produce β-galactosidase of the straits of the invention.

The invention claimed is:

1. A *Kluyveromyces lactis* yeast strain deposited in the Deutsche Sammlung von Mikroorganismen und Zellkulturen GmbH (DSMZ) Culture Collection with deposit number DSM 24900, comprising the sequence identified by SEQ ID NO: 1.

2. Yeast strain according to claim 1, wherein said yeast strain further comprises the sequences identified by SEQ ID NO: 3, 4 and 5.

3. A method for obtaining sugars comprising culturing the *Kluyveromyces lactis* yeast strain of claim 1, in the presence of a lactose-containing medium.

4. Method according to claim 3, wherein said lactose-containing medium is selected from the group consisting of milk, whey, whey resulting from the preparation of butter, whey resulting after casein precipitation, milk permeate, whey permeate, acid whey and YPL culture medium.

5. Method according to claim 3, wherein said sugars are glucose and/or galactose.

6. A method for obtaining ethanol comprising culturing the *Kluyveromyces lactis* yeast strain of claim 1, in the presence of a lactose-containing medium.

7. Method according to claim 6, wherein said lactose-containing medium is selected from the group consisting of milk, whey, whey resulting from the preparation of butter, whey resulting after casein precipitation, milk permeate, whey permeate, acid whey and YPL culture medium.

8. A method for obtaining biomass comprising culturing the *Kluyveromyces lactis* yeast strain of claim 1, in the presence of a lactose-containing medium.

9. Method according to claim 8, wherein said lactose-containing medium is selected from the group consisting of milk, whey, whey resulting from the preparation of butter, whey resulting after casein precipitation, milk permeate, whey permeate, acid whey and YPL culture medium.

* * * * *